(12) United States Patent
Schulz et al.

(10) Patent No.: US 6,611,141 B1
(45) Date of Patent: Aug. 26, 2003

(54) HYBRID 3-D PROBE TRACKED BY MULTIPLE SENSORS

(75) Inventors: Waldean A. Schulz, Boulder, CO (US); Ivan Faul, Boulder, CO (US)

(73) Assignee: Howmedica Leibinger Inc, Kalamazoo, MI (US)

(*) Notice: Subject to any disclaimer, the term of this patent is extended or adjusted under 35 U.S.C. 154(b) by 0 days.

(21) Appl. No.: 09/868,948

(22) PCT Filed: Dec. 22, 1999

(86) PCT No.: PCT/US99/30494
§ 371 (c)(1),
(2), (4) Date: Sep. 17, 2001

(87) PCT Pub. No.: WO00/39576
PCT Pub. Date: Jul. 6, 2000

Related U.S. Application Data

(60) Provisional application No. 60/113,803, filed on Dec. 23, 1998.

(51) Int. Cl.[7] .................... G01B 11/14; A61B 5/05
(52) U.S. Cl. ............... 324/226; 324/207.12; 600/427; 702/94; 356/614
(58) Field of Search ................... 324/226, 227, 324/225, 207.11, 207.12, 207.14, 207.23, 260; 600/427, 425; 356/601, 614; 702/94, 150–153; 250/559.27

(56) References Cited

U.S. PATENT DOCUMENTS

| | | | |
|---|---|---|---|
| 4,323,459 A | 4/1982 | Quinlan | 210/700 |
| 4,396,945 A | 8/1983 | DiMatteo et al. | 358/107 |
| 4,722,056 A | 1/1988 | Roberts et al. | 364/413 |
| 4,869,247 A | 9/1989 | Howard, III et al. | 128/303.1 |
| 4,923,459 A | 5/1990 | Nambu | 606/130 |
| 4,945,914 A | 8/1990 | Allen | 128/653 R |
| 4,951,653 A | 8/1990 | Fry et al. | 128/24 A |
| 4,991,579 A | 2/1991 | Allen | 128/653 R |
| 5,016,639 A | 5/1991 | Allen | 128/653 R |

(List continued on next page.)

FOREIGN PATENT DOCUMENTS

| | | | |
|---|---|---|---|
| DE | 3904595 | 4/1990 | A61B/19/00 |
| EP | 326768 | 8/1989 | A61B/19/00 |
| JP | 3267054 | 11/1991 | A61B/19/00 |
| JP | 6282889 | 10/1994 | G11B/11/10 |
| WO | WO 90/05494 | 5/1990 | A61B/17/22 |

OTHER PUBLICATIONS

Applied Neurophysiology, Journal of Stereotactic and Functional Neurosurgery, Proceedings of the Meeting of the American Society for Stereotactic and Functional Neurosurgery, Montreal, Quebec, (Jun. 3–6, 1987) Jan. 1998.

(List continued on next page.)

Primary Examiner—Walter E. Snow
(74) Attorney, Agent, or Firm—McCracken & Frank

(57) ABSTRACT

This invention is a system that tracks the 3-dimensional position and orientation of one or more bodies (20) in a volume by a light based as well as at least one non-light based mensuration sub-system. This overcomes the limitation of light based mensuration systems to the necessity of the bodies (20) to be in constant line-of-sight of its light based position sensors (26). The invention possesses most of the accuracy and stability of its light based position measurement sub-system (24, 26, 72), but can also work without direct line of sight either for short periods of time or within certain parts of the volume. It does so by incorporating other sensors (31, 34), such as inertial or magnetic, which are frequently recalibrated against the light based sub-system (24, 26, 72) while the bodies (20) are visible by the light based sub-system (24, 26, 72).

55 Claims, 3 Drawing Sheets

U.S. PATENT DOCUMENTS

| | | | | |
|---|---|---|---|---|
| 5,094,241 | A | 3/1992 | Allen | 128/653.1 |
| 5,097,839 | A | 3/1992 | Allen | 128/653.1 |
| 5,119,817 | A | 6/1992 | Allen | 128/653.1 |
| 5,142,930 | A | 9/1992 | Allen et al. | 74/469 |
| 5,178,164 | A | 1/1993 | Allen | 128/898 |
| 5,186,174 | A | 2/1993 | Schlondorff et al. | 128/653.1 |
| 5,198,877 | A | 3/1993 | Schulz | 356/375 |
| 5,211,164 | A | 5/1993 | Allen | 128/653.1 |
| 5,222,499 | A | 6/1993 | Allen et al. | 128/653.1 |
| 5,230,338 | A | 7/1993 | Allen et al. | 128/653 |
| 5,309,101 | A | 5/1994 | Kim et al. | 324/309 |
| 5,383,454 | A | 1/1995 | Bucholz | 128/653.1 |
| 5,394,875 | A | 3/1995 | Lewis et al. | 128/660.09 |
| 5,397,329 | A | 3/1995 | Allen | 606/73 |
| 5,494,034 | A | 2/1996 | Schlondorff et al. | 128/653.1 |
| 5,515,160 | A | 5/1996 | Schulz et al. | 356/241 |
| 5,551,429 | A | 9/1996 | Fitzpatrick et al. | 128/653.1 |
| 5,575,794 | A | 11/1996 | Walus et al. | 606/116 |
| 5,590,215 | A | 12/1996 | Allen | 382/128 |
| 5,595,193 | A | 1/1997 | Walus et al. | 128/898 |
| 5,617,857 | A | 4/1997 | Chader et al. | 128/653.1 |
| 5,622,170 | A | 4/1997 | Schulz | 128/653.1 |
| 5,638,819 | A | 6/1997 | Manwaring et al. | 128/653.1 |
| 5,695,501 | A | 12/1997 | Carol et al. | 606/130 |
| 5,704,897 | A | 1/1998 | Truppe | 600/117 |
| 5,711,299 | A | 1/1998 | Manwaring et al. | 128/653.1 |
| 5,730,130 | A | 3/1998 | Fitzpatrick et al. | 128/653.1 |
| 5,752,513 | A | 5/1998 | Acker et al. | 128/653.1 |
| RE35,816 | E | 6/1998 | Schulz | 356/376 |
| 5,769,789 | A | 6/1998 | Wang et al. | 600/414 |
| 5,797,924 | A | 8/1998 | Schulte et al. | 606/130 |
| 5,799,099 | A | 8/1998 | Wang et al. | 382/131 |
| 5,851,183 | A | 12/1998 | Bucholz | 600/425 |
| 5,871,445 | A | 2/1999 | Bucholz | 600/407 |
| 5,891,034 | A | 4/1999 | Bucholz | 600/426 |
| 5,891,157 | A | 4/1999 | Day et al. | 606/130 |
| 5,907,395 | A | 5/1999 | Schulz et al. | 356/139.03 |
| 5,916,164 | A | 6/1999 | Fitzpatrick et al. | 600/426 |
| 5,921,992 | A | 7/1999 | Costales et al. | 606/130 |
| 5,930,741 | A | * 7/1999 | Kramer | 702/153 |
| 5,954,648 | A | 9/1999 | Van Der Brug | 600/411 |
| 5,970,499 | A | 10/1999 | Smith et al. | 707/104 |
| 5,987,349 | A | 11/1999 | Schulz | 600/427 |
| 6,073,044 | A | 6/2000 | Fitzpatrick et al. | 600/426 |
| 6,081,336 | A | 6/2000 | Messner et al. | 356/375 |
| 6,112,113 | A | 8/2000 | Van Der Brug et al. | 600/427 |
| 6,235,038 | B1 | 5/2001 | Hunter et al. | 606/130 |
| 6,402,762 | B2 | 6/2002 | Hunter et al. | 606/130 |

OTHER PUBLICATIONS

Stereotactic & Functional Neurosurgery vol. 53, No. 3, (1989) pp. 197–201.
Journal of Ultrasound in Medicine vol. 9, No. 9, (Sep. 90), pp. 525–532.
Ultrasound in Neurosurgery J.M. Rubin et al. ISBN: 0881675490, pp. 47–58.
Stereotactic & Functional Neurosurgery vol. 54–55, (1990), pp. 419, 422, 471–476, 482–487, 488–492, 493–496, 497, 498, 500.
British Journal of Neurosugery vol. 4, No. 3, (1990), pp. 193–197.
IEEE Computer Graphics & Applications vol. 10, No. 3, (May 90), pp. 43–51.
Journal of Neurosurgery vol. 72, No. 2, (Feb. 90), pp. 355a.
IEEE Engineering in Medicine & Biology Society—Proceedings of 11th Annual International Conference, (1989), pp. 925, 926–9.
British Journal of Neurosurgery vol. 3, No. 5, (1989), pp. 561–568, 569–574.
British Journal of Neurosurgery vol. 3, No. 3, (1989), pp. 327–331.
Acta Neurochirurgica Supplementum 46, (1989), pp. 112–114.
Journal of Neurosurgery vol. 65, No. 4, (Oct. 86), pp. 550–554, 557–559.
Journal of Neurosurgery vol. 57, No. 2, (Aug. 82), pp. 157–163.
Neurosurgery vol. 10, No. 5, (May 82), pp. 580–586.
Neurosurgery vol. 10, No. 3, (Mar. 82), pp. 375–379.
Guided Brain Operations E.A. Spiegel ISBN: 3805534515, (1982), pp. 23, 25, 28.
American Journal of Neuroradiology vol. 2, No. 2, (Mar./Apr. 81), pp. 181–184.
Neurosurgery vol. 8, No. 1, (Jan. 81), pp. 72–82.
Surgical Neurology vol. 14, No. 6, (Dec. 80), pp. 451–464.
Investigative Radiology vol. 15, No. 4, (Jul./Aug. 80), pp. 308–312.
Applied Neurophysiology vol. 43, No. 3–5, (1980), pp. 170–171, 172–173, 174–175.
Neurosurgery vol. 3, No. 2, (Sep./Oct. 78), pp. 157–161.
Birkfellner et al., "Evaluation and Detection of Systematic Distortions in DC–pulsed Electromagnetic Position Sensing Devices," *Elsevier Science B.V.*, 1998, pp. 927–928.
Birkfellner et al., "Systematic Distortions in Magnetic Position Digitizers," *Med. Phys.* 25 (*11*), pp. 2242–2248 (Nov. 1998).
Livingston et al., "Magnetic Tracker Calibration for Improved Augmented Reality Registration," *Presence*, vol. 6, No. 5, pp. 532–546 (Oct. 1997).
State et al., "Superior Augmented Reality Registration by Integrating Landmark Tracking and Magnetic Tracking," Proceedings of SIGGRAPH 96 (New Orleans, LA, Aug. 4–9, 1996). In *Computer Graphics* Proceedings, Annual Conference Series, pp. 429–438.
Birkfellner et al., "Calibration of Tracking Systems in a Surgical Environment," *IEEE Tansactions on Medical Imaging*, Nov. 17, 1998, pp. 1–6.
Birkfellner et al., "Evaluation of Magnetic Position Digitizers for Computer Assisted Surgery," *Comput. Aided Surg.* 2(3/4), 225 (1997).
Lea et al., "Diagramming Registration Connectivity and Structure" Medical Meets Virtual Reality III (Jan. 1995), pp. 1–10.
Whitaker et al., "Objection Calibration for Augmented Reality" European Computer–Industry Research Centre, (Aug. 1995) pp. 1–18.
Tuceryan et al., Calibration Requirements and Procedures for a Monitor–Based Augmented Reality System, (Jul. 6, 1995) pp. 1–32.

* cited by examiner

HYBRID 3-D PROBE TRACKED BY MULTIPLE SENSORS

This application claims benefit of provisional application No. 60/113,803 filed Dec. 23, 1998.

FIELD OF THE INVENTION

This invention relates to an improvement in systems for measuring the position and orientation of probes and other rigid bodies being tracked in 3-dimensional (3-D) space. The improvements engendered by this invention can be applied to 1-dimensional and 2-dimensional measurement systems, but the description herein describes the invention in the more general context of measurements in three dimensions.

DESCRIPTION OF THE BACKGROUND ART

Various methods and systems exist in the art to track the locations of points (markers) in a spatial volume defined by some 3-D coordinate system. By attaching multiple markers to bodies, even moving bodies, the orientation as well as the position of the bodies, individually or in relationship to each other, can be determined. For example, such bodies may be hand-held probes, moveable rigid objects, or semi-rigid portions of human anatomy.

Hereinafter, the position of a body means its 3-D location plus its 3-D orientation about that location. One common way of expressing this is as X, Y, and Z location coordinates and as yaw, pitch, and roll orientation angles. This is often referred to as six-dimensional information, or six degrees of freedom.)

A number of these methods and systems have been described in previous literature and have been used in practice. The description below will concentrate on light based-electronic tracking methods which use two or more light based sensors to measure the angular locations of markers on an object being tracked with respect to known positions of the sensors in the three dimensional volume. Examples of such prior art techniques are found in the following disclosures, which are herein incorporated by reference:

- H. Fuchs, J. Duran, B. Johnson, and Zvi. M. Kedem; "Acquisition and Modeling of Human Body Form Data", *Proc. SPIE,* v. 166, 1978, p 94–102.
- Jean-Claude Reymond, Jean-Luc Hidalgo; "System for monitoring the movements of one or more point sources of luminous radiation", U.S. Pat. No. 4,209,254, Jun. 24, 1980.
- Y. Yamashita, N. Suzuki, M. Oshima; "Three-Dimensional Stereometric Measurement System Using Light based Scanners, Cylindrical Lenses, and Line Sensors", *Proc. SPIE,* v. 361, 1983, p. 67–73.
- F. Mesqui, F. Kaeser, and P. Fischer; "Real-time, non-invasive recording and 3-d display of the functional movements of an arbitrary mandible point", *SPIE Bio-stereometrics* 602, 1985, p 77–84.
- Sharon S. Welch, Kevin J. Shelton, and James I. Clemmons; "Light based position measurement for a large gap magnetic suspension system", *Proc. of the 37th International Instrumentation Symposium,* San Diego, May 5–9, 1991 p. 163–182.
- Faruhad Daghighian; "Light based position sensing with duolateral photoeffect diodes", Sensors, November, 1994 p. 31–39.
- Robert P. Burton and Ivan E. Sutherland; "Twinkle Box—A three-dimensional computer input device", *AFIPS Conference Proceedings* 43, 1974, Chicago, Ill.

The markers in the above systems emit energy, and typically each marker is an active light source, such as an infrared or visible light emitting diode (LED). Other systems have been constructed to track highly reflective passive markers, and typically each such passive marker is a small patch or sphere coated with retro-reflective material, like that used on highway signs. By illuminating these markers with a light source near the sensors, a larger than normal amount of light is reflected back from the markers to the sensors, making the markers appear brighter than the background or other objects, thereby increasing their visibility and simplifying the process of finding them. Examples of commercial passive 3-D position measurement systems are the following:

The Vector vision system by BrainLAB GmbH (Heimstetten, Germany)

The Peak Motus system by Peak Performance Technologies, Inc. (Englewood, Colo.)

The Eagle Eye ™ system by Kinetic Sciences (Vancouver, British Columbia). However, the limiting problem in all such systems, whether using active or passive light based markers, is maintaining line-of-sight between the markers (reflectors or emitters) and the multiple sensors.

A number of non-light based 3-D measurement systems are known that do not present the line-of-sight limitations. For example, coordinate measurement machines (CMMs) and jointed mechanical arms do not require the marker to be within line of sight of the sensors, but they do require the tactile accessibility of a probe through rigid mechanical linkages, and this generally presents as much of a restriction on the accuracy and ease of operation as line-of-sight limitations. Further, these mechanical means are generally slower and more awkward to use than light based systems. For example, Carl Zeiss IMT Corp. (Minneapolis, Minn.), Romer Inc. (Carlsbad, Calif.), and FARO Inc. (Lake Mary, Fla.) manufacture such systems.

Other three-dimensional measurement systems that avoid the line-of-sight limitations include magnetic field based systems manufactured and sold by Polhemus Inc. (Colchester, Vt.) and Ascension Technology Corp. (Burlington, Vt.). The major drawback to such systems is that their accuracy is considerably degraded by the proximity of conductive objects, especially ferrous metals, and most especially large masses of ferromagnetic, materials, such as X-ray machines and other operating room apparatus. See also U.S. Pat. Nos. 3,983,474, 4,017,858, 5,453,686, and 5,640,170. Improvements have been attempted employing combinations of light based and other mensuration systems. The following reference describes one such combination of a light based and a magnetic tracking system for an image guided surgery application:

Wolfgang Birkfellner, Franz Watzinger, Felix Wanschitz, Rolf Ewers, and Helmar Bergmann; "Calibration of Tracking Systems in a Surgical Environment", *IEEE Transactions on Medical Imaging* 17, (to be published November 1998).

This reference describes calibrating a magnetic system for local anomalies by reference to a light based system before use of the magnetic system. It does not disclose continuous, dynamic registration of multiple (e.g. two) tracking systems during application, as will be discussed below. Furthermore, it does not describe light based tracking of the magnetic system's field source generator.

One very desirable tracking system incorporates at least three built-in, orthogonal, miniature accelerometers and at least three built-in, orthogonal, miniature gyroscopes (or their equivalents) operatively associated with a probe or other tracked body. Such a system is desirable because it assumes that the accuracies of the accelerometers are very precise and that their operations are very stable over time. Unfortunately, to determine the absolute position and angular orientation of the probe or other objects in three dimensional space, their linear and angular acceleration must be integrated twice with respect to time. Furthermore, the slow rotation of Earth continuously affects all the angular measurements that are unaligned with the Earth's poles. In other words, any tiny constant calibration error in the acceleration quickly accumulates into an unacceptably large error. Therefore, the sensors must be recalibrated very frequently, perhaps every minute or two, in order for their accuracy to be acceptable, particularly for medical tracking applications. Therefore, by itself, an inertia-based mensuration system is not very practical for submillimeter measurements and the minute accelerations experienced by a hand-held probe. However, a sufficiently accurate, inertia-based probe would be practical, if it could be recalibrated frequently (or better yet continuously) using some independent reference system.

SUMMARY OF THE INVENTION

Therefore, this invention presents an improvement in position measurement that combines the precision and robustness of light based tracking with another tracking system that does not have the "line of sight" limitations, such as: magnetic or inertial tracking, or ultra-sound, or any combination thereof. The result is a mensuration system that improves the accuracy or freedom of movement of the tracking system combination as compared to any of the individual tracking technologies alone.

The first objective of the present invention is to track the location of a probe or other object using a plurality of physical methodologies in such a way that results achieved by the combination are better than the results achieved using any one of individual constituent methodologies.

A second objective of this invention is to provide an automatic means to use a constituent methodology that has the best accuracy at any particular point in time and/or in space to continuously or frequently recalibrate the other constituent methodology (or methodologies) that have less accuracy at that point.

A third objective of this invention is to provide the operator of the system with a warning when the estimated inaccuracy position and orientation of the probe, or other tracked body or object, exceeds a prescribed limit.

Other and additional objects will become apparent from a consideration of the entirety of this specification, the attached drawing and the appended claims.

To meet these and other objectives, one aspect of the invention comprises a system for tracking the position and orientation of one or more bodies comprising multiple sensors that sense position and orientation and/or movement of the bodies using more than one form of physical phenomena, an associated control unit, and means (preferably automated) to perform geometric computations.

The following paragraphs describe the present invention in terms of two preferred embodiments that employ specific means and a specific method for determining the position and orientation of moveable, substanitially rigid bodies in 3-D space. Alternative means and methods are also mentioned in the text, but other unmentioned, comparable means and methods exist or will be developed that can implement the methods of the invention. All of such comparable means are intended to be embraced by this invention.

BRIEF DESCRIPTION OF THE DRAWINGS

The accompanying figures illustrate two preferred embodiments of the present invention and form a part of the specification. Together with the textual description, these figures serve to explain the advantages and principles of the instant system. Each reference number in the figures consistently refers to the same component of the instant system throughout all the figures and throughout the textual description.

The components in the various figures are numbered as follows:

10 a fixed coordinate system describing a 3-D spatial volume
  12 an optional object being tracked with surface points, dimensions, prominent points, or other geometrical features that could be measured in that volume
  20 at least one whole probe or other body being tracked three-dimensionally
  21 an optional tip for probe 20 for measuring points on optional object 12
  22 a body of a probe (with part broken-away to view part of its inside)
  24 multiple light based detectable markers (such as infrared LED emitters or reflectors of impinged electromagnetic radiation)
  26 an array adapted to sense light beams for tracking the locations of the markers
  31 mutually perpendicular (micromachined) linear accelerometers
  34 mutually perpendicular (micromachined) angular accelerometers
  41 mutually perpendicular magnetic sensors
  44 mutually perpendicular magnetic field sources (coils) shown together in one unit
  47 optional markers sufficient to emit or reflect light beams attached to magnetic field sources
  71 various data/signal paths between a control unit 72 and/or sensors or emitters/reflectors
  72 control unit for power, electronics, signal conditioning, timing, and other support systems
  74 a stream of individual sensor measurements
  75 probe and/or sensor description data (including calibration parameters)
  76 a computational computer (personal computer or embedded microprocessor)
  77 a stream of 3-D position and 3-D orientation coordinates (and optional time data)
  78 host computer hardware and software that utilize the positional and orientation coordinates
  80 the program that controls the system and computes position coordinates
  81 . . . 99 individual steps of program 80 that manage the system

DETAILED DESCRIPTION OF TWO SPECIFIC EMBODIMENTS

The invention will be described below with reference to the figures and the numbered individual components therein. In the description below, the specific construction, the number, and the arrangement of the components are intended for clarity of illustration and are not limitations on the scope of this invention. Other arrangements or quantities of the components constitute alternative specific embodiments of the same method, apparatus and system.

Figure 1:
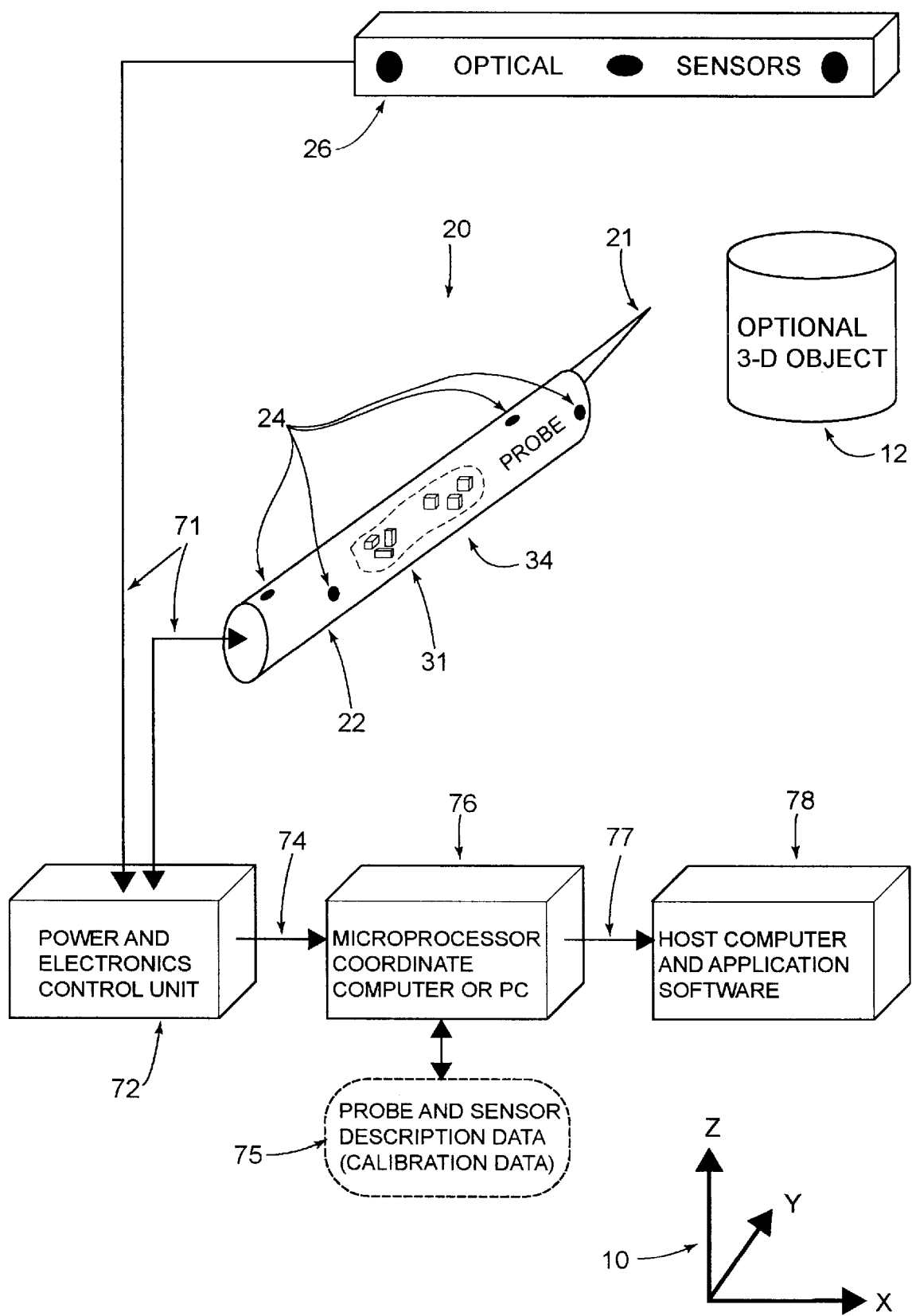
FIG. 1 is a combination of a schematic block diagram and a perspective view of a single object being tracked, that represents a preferred embodiment of the present system, using a combination of light based and inertial subsystems to track the object. The probe is shown enlarged to enable internal detail to be seen.
Figure 2:
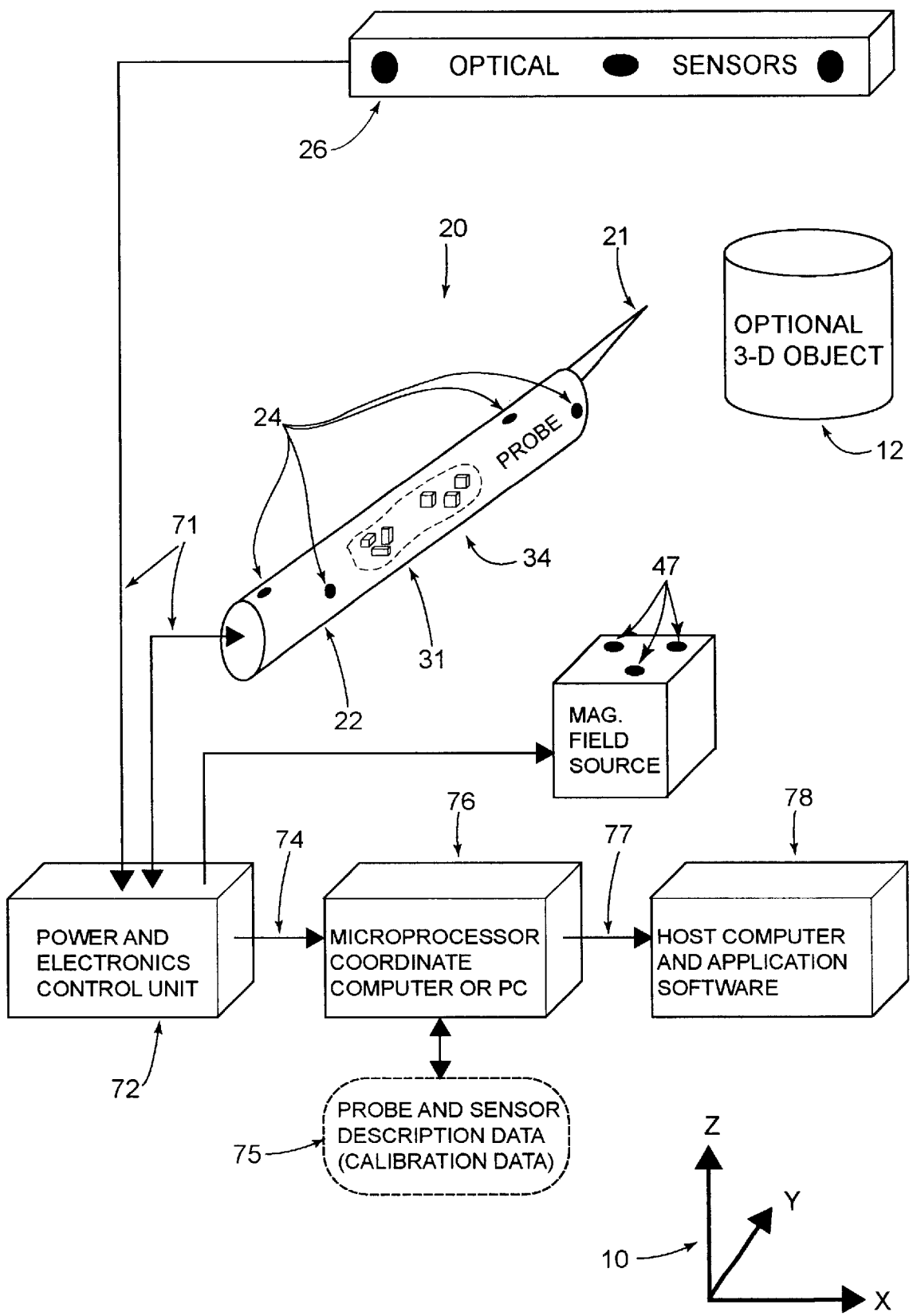
FIG. 2 is similar to FIG. 1 except that a magnetic localizer subsystem has been substituted for the inertial subsystem of FIG. 1. The probe is shown enlarged to enable internal detail to be seen.
Figure 3:
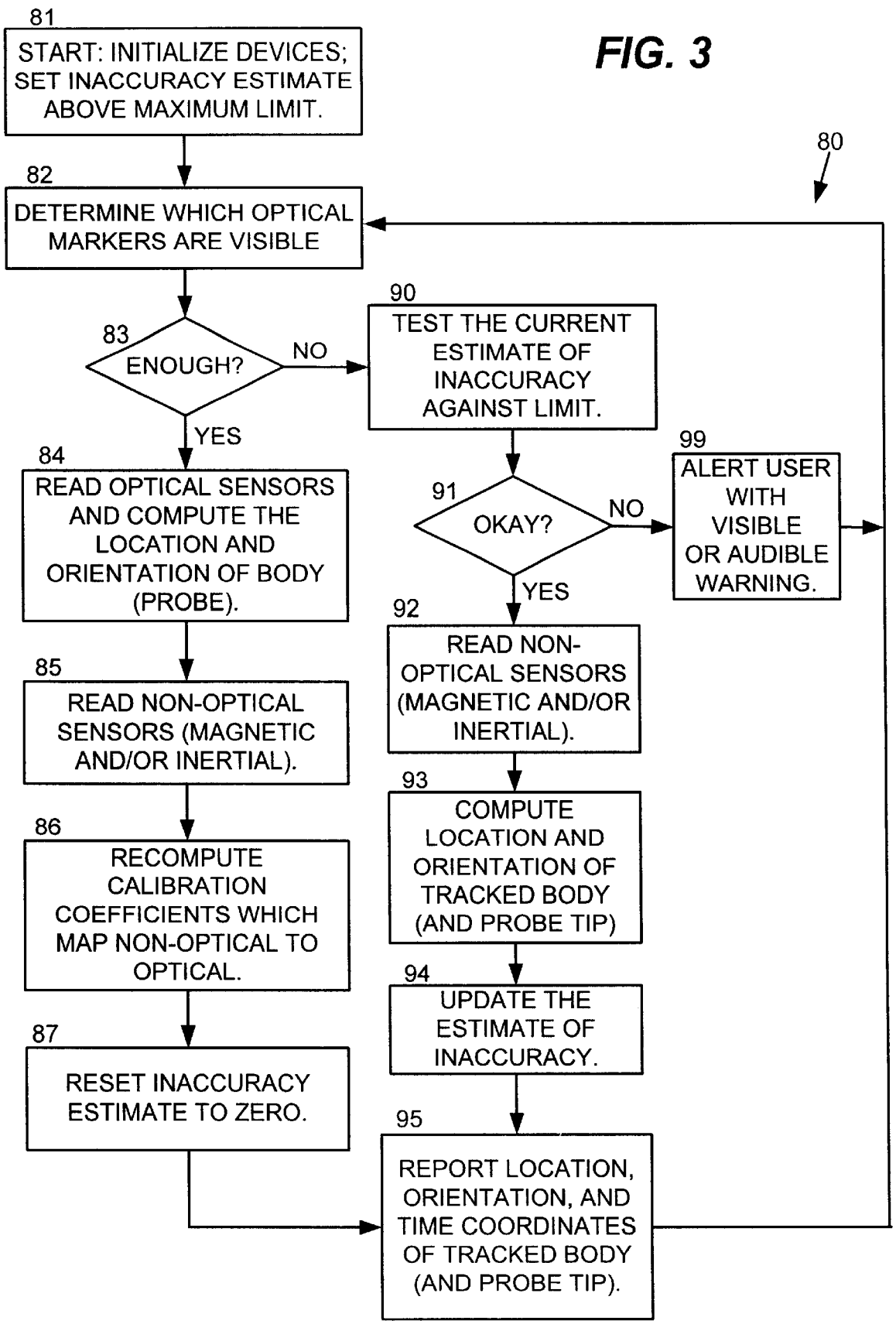
FIG. 3 is a flow chart that outlines one preferred set of major steps of operation and computation performed by a coordinate computer for either of the preferred embodiments or for a combination thereof.

FIGS. 1 and 2 illustrate two alternative preferred embodiments of the present invention. FIG. 3 depicts as a flowchart the major steps 81 . . . 99 of the program that operates the coordinate computer 78 and other peripheral equipment. These program steps apply to either or both of the two embodiments and even to an embodiment that combines the components of those two.

With reference to FIG. 1, the apparatus includes a 3-D light based measurement system, such as the FlashPoint 5000 built by Image Guided Technologies, Inc., of Boulder, Colo. The electromagnetic radiation sensors 26 detect the image of each light emitting or reflecting marker 24 on the probe or other body 20, where each marker is a light emitting diode (LED) or a passive reflector. The locations of the images of the markers are sent to a control unit 72 via a transmission means (such as a wire or wireless radio) 71. The control unit 72 processes each image into sensor coordinates and transmits the same, via line 74, to a coordinate computer 76 that computes the 3-D XYZ coordinates of each marker 24 using the sensor coordinates from all the sensors 26 and using calibration parameters 75. The actual means of determining the location of a marker (emitter or reflector) is described in U.S. Pat. No. 5,622,170, the entirety of which is incorporated herein by reference. Note that more markers 24 than shown in FIG. 1 may be used and not all markers need to be seen at the same time by the light based sensors 26. At least three non-collinear markers must be detected by the sensors 26 in order to fully determine the 3-D position and 3-D orientation of the probe. If the sensors are one dimensional, three sensors must detect the emissions or reflections. If the sensors are two dimensional, at least two sensors must detect the emissions or reflections. If the sensors are thre dimensional, only one sensor needs to be intersected by emissions or reflections of electromagnetic energy. In the case of a probe of known geometry, a further simple computation could be used to determine the location of the probe tip 21 that is in a fixed position relative to the markers.

If there is no explicit probe tip 21 that needs to be determined, then the position and orientation of the body 20 being tracked would be with respect to some reference location on the body, such as one of the markers 24. The details enabling the performance of these individual steps are disclosed in the references cited above.

In the preferred embodiment of FIG. 1 the body also houses multiple linear accelerometers 31, such as the ADXL202 manufactured by Analog Devices, Inc. At least one accelerometer 31 should be aligned with each of the body's three dimensional axes.

Furthermore, the embodiment may also include a plurality of angular accelerometers 34 (also known as solid state or piezoelectric gyroscopes). For example, three accelerometers can be used. Examples of such devices are the G-2000 manufactured by Litton Guidance & Control Systems (Salt Lake City, Utah) or the Gyrostar by MuRata Erie (Smyrna, George). These manufacturers publish drift specifications that disclose how long the angular accelerometers 34 will perform within the required orientation accuracy before needing recalibration.

One way to calibrate the non-light based sensors with respect to the light based system is to calculate the rigid linear transformation that relates the 3-D position as determined by the non-light based sensors to the 3-D position, as determined by the light based system. A rigid linear transformation is commonly described as a rotation R about some axis through the origin followed by a translation (shift) S in 3-D space. The rotation may be described as a sequence of yaw, pitch, and roll angles or as Euler angles. However, it is generally more convenient to use either a quaternion or an orthonormal 3-by-3 matrix R to represent the rotation. The translation S is represented by a 3-D vector. So, for example, a coordinate triple [X' Y' Z'] computed by the non-light based subsystem is related to a coordinate triple [X Y Z] computed by the light based subsystem as follows:

$$[XYZ] = [X'Y'Z'] \cdot R + S$$

where · is matrix multiplication and + is vector addition.

For details, see any college text on linear algebra, or see *Computer Graphics: Principles and Practice* by Foley, van Dam, Feiner, and Hughes (Addison Wesley, New York, 1990).

As the non-light based sensors 31, 34 drift or exhibit bias, the numbers in the linear transformation will slowly vary. Sometimes the variance is at a substantially constant rate. By keeping track of the rate of change (rotation and translation) with respect to time and/or temperature and/or other environmental factors, the system can internally estimate the inaccuracy of the non-light based sensor.

While sufficient light based markers are in line-of-sight of the light based sensors, the linear transformation is frequently recomputed. When insufficient markers become visible to the sensors, the last-computed transformation is used to correct the positional computations from the other, non-light based, e.g. inertial, subsystem. In a more preferred system, the linear transformation is continually altered at the same rate at which it had been most recently changing. This usually will allow the non-light based system to operate more accurately for a longer time because the inaccuracy that is most recently known from accurate light based tracking is being extrapolated using the most recent rate of change of inaccuracy.

When the extrapolated inaccuracy exceeds some user-defined limit (program Step 91) and a sufficient number of light based markers on the tracked body are out of line-of-sight, then the user is preferably notified of this condition, suitably by an audible or visible indicator (program Step 99). Coordinate data could still be produced by the micro processor 76 and recorded, but is immediately suspect, and a wanting indicator (such as a bad status code) is preferably associated with the questionable data that are being generated.

As shown in FIG. 2, a second preferred embodiment of this invention also includes 3-D light based sensors 26 and whatever circuitry in the control unit 72 is required for support. However, the linear and angular accelerometers 31, 34 unlike the system of FIG. 1, are replaced with magnetic sensors 41 that are preferably, but not necessarily, located in the body 20. Also, a steerable magnetic field source 44 is provided. The location of the several sensors 41 can thus be determined, and from these locations the position and orientation of the body 20 (or bodies) with which they are associated can be deduced. Such a sub-system is exemplified by the products referred to above as being manufactured and sold by Polhemus or Ascension.

In the simplest and most preferred implementation of this embodiment of this invention, the magnet field source 44 remains physically stationary and light based markers 47 are not used. (The magnetic field source 44, however, is steered electronically.) As the probe or other body 20 is moved farther away from the magnetic field source 44, the mensuration accuracy decreases at a geometric rate that is proportional to the distance. Beyond a predetermined distance, the inaccuracy introduced by the distance of the body from the magnetic source exceeds its accuracy limit. If a sufficient number of light based markers on the body 20 are visible to the light based sensors, the 3-D coordinates can be produced anyway using the light based sensor information alone. So the optimal location of the magnetic source 44 is proximate to locations where the body will be light based obscured, but where the magnetic based subsystem is most accurate. The body may then be tracked into the obscured volume, such as inside a medical patient during a catheter procedure.

A more preferred implementation of the embodiment of FIG. 2 employs additional light based markers 47 on the magnetic field source 44. Assuming that a least 3 non-collinear markers 47 are visible to the light based sensors 26, the position and orientation of the magnetic field source 44 can be determined in just the same way as any other body, such as object 20. Unlike the simpler implementation described in the previous paragraph, the magnetic field source 44 can then be moved dynamically while its position and orientation are still being tracked. It will always be moveable to a position and orientation at which it is visible to the light based sensors 26 and yet be close enough to the magnetic sensors 41 to allow the generation of sufficient magnetic based data to relatively accurately determine coordinates even when the markers 24 on the body 20 are not in a line of sight with the light based sensors. In this case, the linear transformation relating the magnetically derived XYZ coordinates to the light derived XYZ coordinates must include the linear transformation between the moveable magnetic field source 44 and the fixed light based sensors 26. This is not unlike the transformation required in U.S. Pat. No. 5,198,877 (incorporated by reference), in which the locations of points are determined relative to a freely moveable 3-D measurement system, which is itself tracked by another 3-D measurement system.

Note that it is theoretically possible in the above described system to interchange the cluster of magnetic sensors 41 with the magnetic source 44, because the 3-D measurement simply tracks one magnetic component relative to the other. However, the magnetic source is generally larger and bulkier and not well suited to be incorporated in a hand-held probe. Furthermore, the system would then be limited to tracking only one body 20, the body holding the magnetic source. For similar reasons, it is theoretically possible, but perhaps impractical, to interchange the roles of the light based sensors and the light based markers/reflectors.

Note that the systems of FIG. 1 and FIG. 2 are not mutually exclusive. It is possible to provide a probe containing both accelerometers and magnetic sensors (or even yet other position measurement systems, such as ultra sound transducers). When a sufficient number of light based markers on a probe are within view of the light based sensors, both of the non-light based subsystems are continuously recalibrated. When insufficient markers are visible, then one or both non-light based sensor sub-systems are used to determine the position and orientation of the body (probe). Each sub-system provides an internal estimate of its own inaccuracy. If only one estimate exceeds the limit, then the data from the other sub-system is used. If neither exceeds the limit, then either sub-system can be used or the (weighted) average of the coordinates produced by the two subsystems can be used. If neither sub-system is within acceptable inaccuracy limits, the results reported by the system are suspect and should be flagged.

With reference to FIG. 3, the operation of the present invention begins in Step 81 by initializing the light based and inertial/magnetic sub-systems and by initializing the inaccuracy estimate for these non-light-based sub-systems to an unacceptably large value in order to force the system to calibrate the non-light based sub-system(s) to the reference light based subsystem, after which the inaccuracy is reset to zero in Step 87. (That is, the large initial inaccuracy estimate will alert the user in Step 99 to place the body in a position where the light based subsystem is operational, if that is not already the case.) Steps 82 and 83 determine whether the light based sensors can see enough of a body's markers 24 to make a reliable 3-D position measurement of the body 20. If so, Step 84 performs the measurement as well as computing the location and direction of the tip 21 if it exists and if it is desired. Step 85 does the same using the non-light based sub-system(s). Step 86 relates these two measurements to each other by using an orthonormal linear transformation as described above or using some other method. Step 87 resets the inaccuracy limit to zero (or some other small appropriate estimate). Lastly, Step 95 reports the coordinates derived from information provided by the light based sensors 26 through the microprocessor 76 and to the host computer 78 before the cycle repeats at Step 82. Note that the coordinate reports could be accompanied by reports of the non-light based coordinates too, the inaccuracy estimate, a time stamp, and a "success" status code.

If the light based system cannot see enough markers 24 on a body 20, then Steps 90 and 91 are adapted to check the current other non-light based sub-system inaccuracy estimate. If it exceeds a preset limit, then the user is preferably visually or audibly warned about this condition in Step 99. Although not shown, the coordinates could still be reported by Step 95, but some "warning" status code should be attached to the data. If the inaccuracy estimate of the other non-light based sub-system is within the limit, Step 92 reads that non-light based sensors 31, 34, and/or 41, and Step 93 computes the position and orientation of the body 20 and the location and direction of its tip 21, if appropriate. Step 94 updates the current other non-light based subsystem estimated inaccuracy based on elapsed time since Step 87 was executed or based on distance of the body 20 from the magnetic source 44 or based on other environmental factors like temperature. Step 95 reports the position coordinates derived from the non-light based sensors 31–34 and/or 41 and continues to repeat the cycle again at Step 82.

The principles of this invention may be applied to measurement technologies beyond the magnetic and inertial technologies discussed in detail in the foregoing preferred embodiments.

For example, a previous U.S. patent application Ser. No. (60/096,907) has described a non-line-of-sight flexible shaft method of determining 3-D points or tracking a body. If, for illustration, that method suffers from bad accuracy in certain parts of its measurement volume or if the accuracy degrades as the shaft is flexed over time or during temperature changes, auxiliary light based or other subsystem could be employed to recalibrate the flexible shaft frequently whenever the probe end of the shaft (equipped with visible markers) is in view of the light based sensors.

The above description is based on the use of light based sensors as the primary (reference) position measurement subsystem. However, any type of position sensor can be used as the primary position measurement system. Any primary system can be combined with any one or more secondary measurement system such as a combination of inertial and magnetic subsystems. In an appropriate case, the magnetic subsystem could be used to correct the inertial subsystem from time to time, or vice versa. The advantage of this combination is that the inertial system can be used for short periods of time at a distance that is beyond the higher-accuracy available by the magnetic sensors being close to the magnetic source.

What is claimed is:

1. A system to track the three-dimensional position of an object within a defined volume comprising:
   a first tracking system to determine a first indication of the position of the object;
   a second tracking system independent of the first tracking system to determine a second indication of the position of the object;
   a first circuit operative to compare the first indication of the position with the second indication of the position of the object;
   a second circuit coupled to the first circuit and operative to determine a variance between the second indication of the position of the object and the first indication of the position of the object; and
   a third circuit coupled to the first and second circuits and operative to update the variance.

2. The system of claim 1 wherein the variance is estimated if one of the first indication of the position of the object or the second indication of the position of the object cannot be determined.

3. The system of claim 1, wherein the first tracking system is electromagnetic.

4. The system of claim 3, wherein the electromagnetic system uses energy in the visible spectrum.

5. The system of claim 3, wherein the electromagnetic system uses energy in the infrared spectrum.

6. The system of claim 1, wherein the second tracking system is magnetic.

7. The system of claim 1, wherein the second tracking system is inertial.

8. The system of claim 1, wherein the system also comprises a fourth circuit coupled to the third circuit and operative to provide a warning if the variance exceeds a predetermined limit.

9. The system of claim 1, wherein the system also includes a fourth circuit coupled to the first and second circuits and operative to determine which of the first tracking system or the second tracking system is more accurate and which of the first tracking system or the second tracking system is less accurate.

10. The system of claim 9, wherein the system also includes a fifth circuit coupled to the fourth circuit and operative to calibrate the less accurate system to the more accurate system.

11. A method of guiding an object during a medical procedure, the method comprising the steps of:
   providing a first tracking system to determine a first indication of the position of the object;
   providing a second tracking system independent of the first tracking system to determine a second indication of the position of the object;
   comparing the first indication of the position of the object and the second indication of the position of the object to determine a variance;
   estimating a variance between the first indication of the position of the object and the second indication of the position of the object; and
   updating the estimate of the variance.

12. The method of claim 11, wherein step of estimating of the variance is conducted if one of the first indication of the position of the object or the second indication of the position of the object cannot be determined.

13. The method of claim 11, wherein the first tracking system is electromagnetic.

14. The method of claim 13, wherein the electromagnetic system uses energy in the visible spectrum.

15. The method of claim 13, wherein the electromagnetic system uses energy in the infrared spectrum.

16. The method of claim 11, wherein the second tracking system is magnetic.

17. The method of claim 11, wherein the second tracking system is inertial.

18. The method of claim 11, wherein the system also comprises a step of warning if the variance exceeds a predetermined limit.

19. The method of claim 11, wherein the method also includes the step of determining which of the first tracking system or the second tracking system is the more accurate and which of the first tracking system or the second tracking system is less accurate.

20. The method of claim 19, wherein the method also includes the step of calibrating the less accurate system to the more accurate system.

21. A system to track the three dimensional position and orientation of an object within a defined space comprising:
   an electromagnetic tracking system to determine the electromagnetic position and orientation of this object;
   an inertial tracking system to determine the inertial position and orientation of the object;
   means for comparing the electromagnetic position and orientation of the object and the inertial position and orientation of the object; and
   means for estimating the variance of the inertial position and orientation of the object from the electromagnetic position and orientation of the object.

22. The system of claim 21 wherein the system further includes means for updating the variance estimate.

23. The system of claim 22, wherein the variance is estimated if the electromagnetic position of the object cannot be determined.

24. The system of claim 21, wherein the electromagnetic system uses energy in the visible spectrum.

25. The system of claim 21, wherein the electromagnetic system uses energy in the infrared spectrum.

26. The system of 21 wherein the system also comprises a means for warning if that variance estimate exceeds a predetermined limit.

27. The system of claim 21, wherein the system further includes a second circuit coupled to the first-named circuit and operative to determine which of the electromagnetic tracking system or the inertial tracking system is more accurate and which of the electromagnetic tracking system or the inertial tracking system is less accurate.

28. The system of claim 27, wherein the system further includes a third circuit coupled to the first-named circuit and the second circuit and operative to calibrate the less accurate system to the more accurate system.

29. A system to track the three-dimensional position of an object within a defined volume comprising:
   a first tracking system to determine a first indication of the position of the object;

a second tracking system independent of the first tracking system to determine a second indication of the position of the object;

a first circuit operative to compare the first indication of the position with the second indication of the position of the object;

a second circuit coupled to the first circuit and operative to determine which of the first tracking system or the second tracking system is more accurate and which of the first tracking system or the second tracking system is less accurate; and a third circuit coupled to the first and second circuits and operative to calibrate the less accurate system to the more accurate system.

30. The system of claim 29, wherein the system further includes a fourth circuit coupled to the first circuit and operative to determine a variance between the first indication of the position of the object and the second indication of the position of the object.

31. The system of claim 30, wherein the system further includes a fifth circuit coupled to the fourth circuit and operative to update the variance.

32. The system of claim 30, wherein the variance is updated if one of the first indication of the position of the object or the second indication of the position of the object cannot be determined.

33. The system of claim 29, wherein the first tracking system is electromagnetic.

34. The system of claim 33, wherein the electromagnetic system uses energy in the visible spectrum.

35. The system of claim 33, wherein the electromagnetic system uses energy in the infrared spectrum.

36. The system of claim 29, wherein the second tracking system is magnetic.

37. The system of claim 29, wherein the second tracking system is inertial.

38. The system of claim 30, wherein the system further includes a fifth circuit coupled to the fourth circuit and operative to warn if the variance exceeds a predetermined limit.

39. A system for determining a position of an object in a three dimensional volume, comprising:

an electromagnetic position determination system operative to develop a first indication of the position of the object based on a line-of-sight detection of electromagnetic energy;

a non-line-of-sight position determination system operative to develop a second indication of the position of the object;

a first circuit operative to compare the first indication to the second indication;

a second circuit coupled to the first circuit and operative to provide an electromagnetic position determination system accuracy estimate and a non-line-of-sight position determination system accuracy estimate; and a third circuit coupled to the second circuit and operative to develop a warning when the accuracy estimate for either system exceeds a predetermined limit.

40. The system of claim 39, further including a fourth circuit coupled to the first circuit and operative to calibrate the non-line-of-sight position determination system to the electromagnetic position determination system.

41. The system of claim 39, wherein the electromagnetic position determination system also develops a first indication of the orientation of the object and the non-line-of-sight position determination system also develops a second indication of the orientation of the object.

42. The system of claim 39, wherein the second circuit is also operative to track the accuracy estimate of the non-line-of-sight position determination system while the electromagnetic position determination system is functioning; and to apply a correction to the position of the object as determined by the non-line-of-sight position determination system when the electromagnetic position determination system is unable to accurately determine the position of the object.

43. The system as claimed in claim 39, wherein the electromagnetic system uses energy in the infrared spectrum.

44. The system as claimed in claim 39, wherein the electromagnetic system uses energy in the visible spectrum.

45. The system as claimed in claim 39, wherein the non-line-of-sight position determination system is magnetic.

46. The system as claimed in claim 45, wherein the magnetic non-line-of-sight position determination system comprises at least three orthogonally disposed magnetic flux detectors.

47. The system as claimed in claim 39, wherein the non-line-of-sight position determination system is inertial.

48. The system as claimed in claim 47, wherein the inertial non-line-of-sight position determination system comprises a plurality of accelerometers.

49. The system as claimed in claim 48, wherein the inertial non-line-of-sight position determination system comprises at least three orthogonally disposed accelerometers.

50. The system as claimed in claim 39, further comprising a second non-line-of-sight position determination system.

51. The system as claimed in claim 50, wherein the non-line-of-sight position determination systems are inertial and magnetic, respectively.

52. The system as claimed in claim 39, wherein the first circuit is further operative to average the first indication and the second indication.

53. The system as claimed in claim 39, wherein the electromagnetic position determining system further comprises a source of electromagnetic energy that is spaced from the object and wherein the object includes reflectors of the electromagnetic energy radiated from the source.

54. A system for determining a position of an object in a three dimensional volume, comprising:

an electromagnetic position determination system operative to develop a first indication of the position of the object based on a line-of-sight detection of electromagnetic energy; and a magnetic position determination system operative to develop a second indication of the position of the object;

wherein the magnetic position determining system includes an independent magnetic field generator spaced from the object, magnetic flux detectors disposed in operative relationship to the object and within operative distance from the magnetic field generator, and electromagnetic energy emitters operatively associated with the magnetic field generator to enable the determination of the position of the magnetic field generator by the electromagnetic position determining system.

55. The system as claimed in claim 54, wherein the generator can be moved into a position whereby at least some of the emitters are a in line-of-sight relationship with the electromagnetic sensors to enable the determination of the position of the generator, and whereby the magnetic sensors operatively associated with the object are sufficiently within the magnetic flux emitted by the generator to provide accurate determinations of the position of the object.

* * * * *